(12) United States Patent
Villafana

(10) Patent No.: US 6,241,761 B1
(45) Date of Patent: Jun. 5, 2001

(54) STENTED GRAFTS FOR COUPLING VASCULAR MEMBERS

(75) Inventor: Manuel A. Villafana, Minneapolis, MN (US)

(73) Assignee: CABG Medical, Inc., Plymouth, MN (US)

(*) Notice: Subject to any disclaimer, the term of this patent is extended or adjusted under 35 U.S.C. 154(b) by 0 days.

(21) Appl. No.: 09/525,195

(22) Filed: Mar. 14, 2000

Related U.S. Application Data

(63) Continuation-in-part of application No. 09/491,566, filed on Jan. 26, 2000.

(51) Int. Cl.$^7$ ........................................................ A61F 2/06
(52) U.S. Cl. ........................ 623/1.13; 623/1.16; 623/1.27; 623/1.35
(58) Field of Search .................................. 623/1.27, 1.35, 623/1.16, 1.13, 12; 606/190, 194; 604/8

(56) References Cited

U.S. PATENT DOCUMENTS

| | | | |
|---|---|---|---|
| 5,443,497 * | 8/1995 | Venbrux | 623/1 |
| 5,453,084 | 9/1995 | Moses . | |
| 5,562,726 * | 10/1996 | Chuter | 606/195 |
| 5,588,436 | 12/1996 | Narayanan et al. . | |
| 5,797,879 | 8/1998 | DeCampli . | |
| 5,807,258 | 9/1998 | Cimochowski et al. . | |
| 5,824,064 | 10/1998 | Taheri . | |
| 5,922,022 * | 7/1999 | Nash et al. | 623/12 |
| 5,967,989 | 10/1999 | Cimochowski et al. . | |
| 5,968,053 | 10/1999 | Revelas . | |
| 5,984,956 * | 11/1999 | Tweden et al. | 623/1 |
| 5,989,192 | 11/1999 | Weijand et al. . | |

* cited by examiner

Primary Examiner—Gary Jackson
(74) Attorney, Agent, or Firm—Haugen Law Firm PLLP

(57) ABSTRACT

Improved stented grafts for coupling vascular members, and for use in surgical implantation during coronary bypass operations. The stented graft of the present invention comprises a plurality of graft link segments, each having a lumen for accommodating blood flow, and with at least one graft link segment being secured to one end of a vascular stent forming a junction between a supply lumen and a delivery lumen. The delivery lumen is arranged to be inserted into the patient's vascular system downstream from blockage in the coronary artery. In order to provide ease of access for the attachment of a second graft link segment to the stent assembly, the individual tubular element or elements defining the dual lumen assembly are axially offset, one from the other, in order to expose the free end of the stent for receiving a second graft link segment.

3 Claims, 3 Drawing Sheets

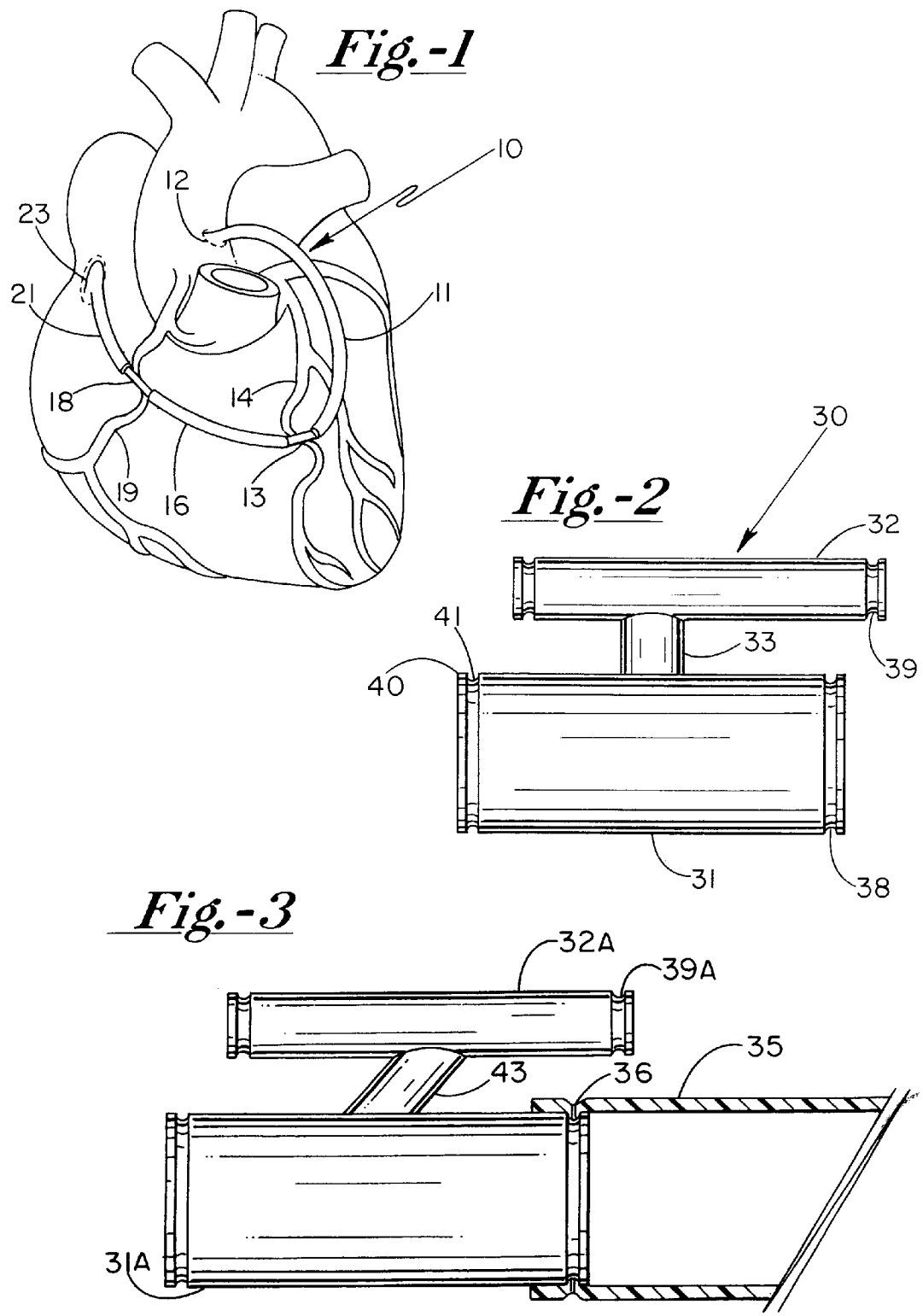

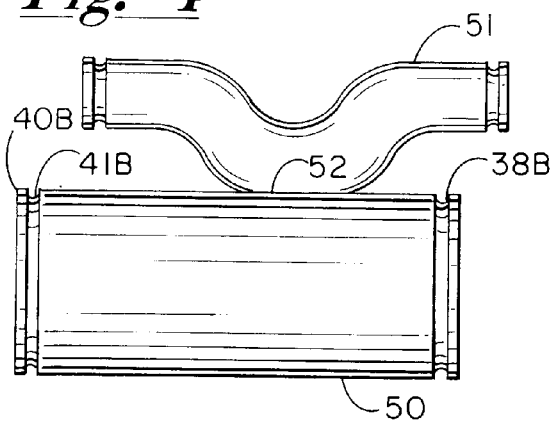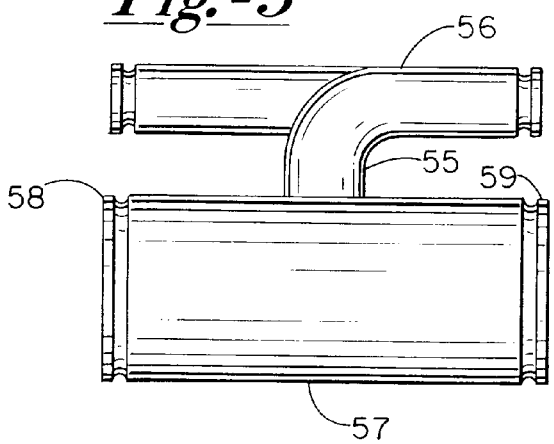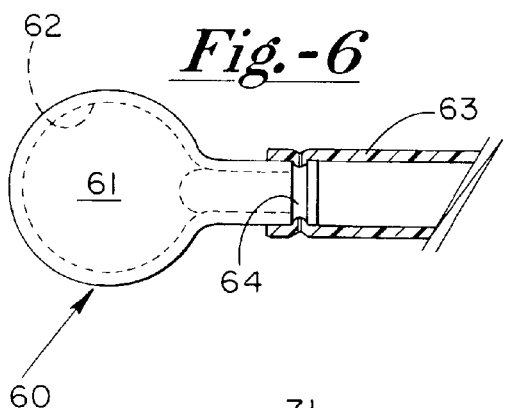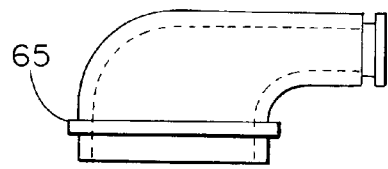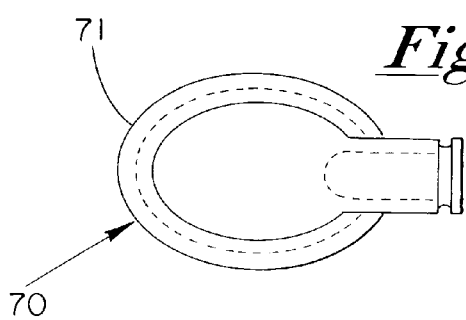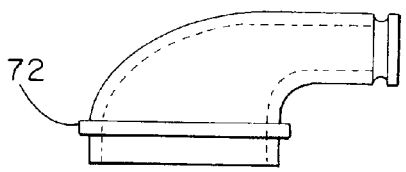

STENTED GRAFTS FOR COUPLING VASCULAR MEMBERS

CROSS-REFERENCE TO RELATED APPLICATION

The present application is a continuation-in-part of my co-pending application Ser. No. 09/491,566, filed Jan. 26, 2000, entitled "STENTED GRAFTS FOR COUPLING VASCULAR MEMBERS", and assigned to the same assignee as the present application.

BACKGROUND OF THE INVENTION

The present invention relates generally to an improved vascular graft system, and in particular to a stented vascular graft system incorporating improved stents and grafts designed to provide flow transfer from an aortic source to a branch flow path for coronary bypass procedures. In accordance with the present invention, graft material is appropriately secured to the stent structure so as to facilitate this step in the coupling of the graft system to the vasculature of the patient, thereby expediting the surgical procedure while at the same time reducing the number of suturing steps necessary in the procedure. The features of the present invention are set forth in greater detail hereinafter.

Coronary bypass surgery has become a common procedure, and is normally indicated for conditions requiring replacement and/or reconfiguration due to blockage of the coronary blood flow within a patient. Apparatus and techniques are also disclosed herein for selectively monitoring the flow through a graft. The present invention involves use of a stented graft, and particularly wherein the stent is utilized to receive the graft and also for modifying the flow pattern through coupling to relevant portions of the vasculature. Two forms of stented grafts are utilized in a typical surgical procedure, with a first form being employed for introduction into a coronary artery downstream from a blockage site, and with the second form of stented graft being employed to couple the distal end of the graft network to a point of relatively lower flow pressure, and to serve as a terminus for the grafted structure. In the second form of stented graft, means are provided for suturing the stent to a selected location, typically at the right atrium or superior vena cava. The utilization of stented grafts facilitates and expedites the procedure while reducing the number of necessary steps, all of this being achieved without compromising the efficacy of the overall procedure.

In a typical bypass procedure, a section of the vascular system in a patient's body that has become impaired or inoperative through disease or other defect may be treated so as to improve flow to those portions previously being given an inadequate or limited supply of blood. In order to create the graft network, biocompatible graft material may be employed, such as, for example, Gortex™, with this being a polytetrafluoroethylene-based material normally being accepted by the patient's body. Thus, such graft material is frequently and typically utilized in bypass as well as in other procedures such as, for example, as a joint reinforcing material, such as a brace interposed across the knee.

Because of the physical properties of the biocompatible graft material, stent suturing, while possible, is frequently difficult to complete. The procedure is one which requires great dexterity, and when done at the site, is frequently in a zone with limited accessibility. In the design of the stent portion of the stented grafts, a certain degree of axial offset is provided in order to more fully and completely expose a portion of the stent to which a graft must be applied during the surgical procedure. Because of this greater accessibility and visibility, the stented graft device of the present invention is highly desirable.

Coronary bypass procedures are frequently undertaken with patients whose coronary arteries have been partially or almost completely blocked, thereby impeding and disrupting the proper flow of blood through the vascular system. While bypass procedures have been undertaken for some period of time, one meticulous and time consuming step is that of suturing the vascular graft elements. The time required for completing each such suture is reduced significantly through providing a pre-attached or stented graft in accordance with the present invention.

As a further feature of the present invention, means can be provided in combination with the vascular assembly for monitoring blood flow through various branches of the graft configuration. In particular, flow rate monitoring may be achieved through utilization of devices functioning in response to temperature variations resulting by introducing a temperature energy signal into the bloodstream, and measuring and/or detecting the thermal response at a downstream location. Another technique suitable for use in connection with the present invention is based upon the use of ultrasonic signals, wherein the system comprises one or more signal generators in communication with the blood flow (transducers) along with detection means, normally an array transducer exposed to the signal. Doppler techniques may be employed to determine flow rate and volume. Such systems are known in the art, with a thermal response system being disclosed in U.S. Pat. No. 5,989,192, and with ultrasonic systems being disclosed in U.S. Pat. No. 5,967,989; 5,807,258 and 5,588,436.

In order to evaluate the condition of an individual graft, determinations of flow velocity and overall blood volume provide a good indicator. A determination of pressure differentials between opposed ends of a graft will provide valuable information as well. Obviously, as deposits collect along the interior wall of a graft, pressure differentials will increase along with a corresponding decrease in velocity and flow volume. The utilization of the stented grafts in accordance with the present invention reduces some of the potential for buildup within certain other graft structures, this being accomplished by tailoring the configuration of the flow channel through the stent so as to preserve flow patterns, and also preserve and/or reduce the tendency for any increase in the Reynold's number within the blood flow through the graft network.

SUMMARY OF THE INVENTION

In accordance with the present invention, a family of stented grafts are provided for each bypass procedure. In addition to the terminal stent to be described hereinafter, at least one branch stent is provided for each procedure, with the branch stent comprising biocompatible material and including a feature for cross-flow from the supply channel which communicates with the aorta to a location in the coronary artery where flow correction is needed. This location is typically downstream of the blockage necessitating the bypass procedure. These stent devices are typically dual lumen with a cross-flow channel being provided between the lumens, thus permitting a portion of the blood from the main supply to be utilized for flow to the blockage site. In the dual lumen structure, a relatively large diameter lumen is employed for that portion of the graft which is in direct communication with the aorta, with the second lumen typically being of somewhat lesser overall diameter and being designed for insertion into a slit formed in the coronary artery requiring bypass. For many applications, a lumen diameter of approximately 2 mm. is desirable and useful, although lumens of slightly larger and/or smaller diameter may be appropriately considered.

The stented grafts also include a terminal or distal stent structure which is designed to be coupled directly to the terminus of the graft network, such as at the right atrium or superior vena cava. This terminal member includes a biocompatible body having a channel or bore therethrough which is provided with a suture flange at one end, and with a graft being secured to the other. As indicated above, the configuration of the bore is such that the flow rate is maintained consistent with that through the balance of the supply network, with the Reynold's number being held well within the laminar area.

In each instance, the graft material is pre-attached to the stent and is of a length which is more than ample for the contemplated use. Thus, the surgeon is able to cut the graft to a desired and required length in the course of the procedure, while at the same time, not having to disturb the integrity of the previously prepared secure junction between the stent and the graft. In the course of the overall procedure, therefore, the distal end of the bypass network including the graft segment along with an appropriate clamping network is secured in place at the vena cava or other low-pressure site, while continuing the process in the direction of the source, normally the aorta. The attachments are made in accordance with the conventional protocol fashion. The first stent is coupled through a slit formed in the pertinent vessel to provide bypass flow through a terminal stent to be described hereinafter. Thereafter, the graft portion of a second stented graft is cut to length, and thereafter sutured to the upstream side of the supply channel of the stent. When there is need for a bypass to one or more additional coronary arteries, an additional or second stent will be attached to each further diseased artery in the same fashion as indicated above. Finally, the stented graft utilizing the stent to be coupled to the upstream side of the supply channel is cut to length and appropriately secured and sutured to the right atrium and/or superior vena cava.

Therefore, it is a primary object of the present invention to provide an improved stented graft which is designed for use in graft networks for bypass procedures, and wherein the graft network is surgically implanted within the body of a patient, typically within the thorax.

It is a further object of the present invention to provide an improved stented graft wherein the graft is securely attached and coupled to the upstream end of the supply channel of a dual lumen stent, and wherein an internal cross-over is provided which permits metered flow of blood from the supply lumen to the coronary artery at a zone adjacent the diseased or impaired area of the artery.

It is a further object of the present invention to provide a family of dual stents which incorporate a supply lumen or channel portion along with a delivery lumen or channel portion, and wherein a separate cross-over lumen is provided for enabling blood flow from the supply channel to the delivery channel, and wherein the configuration of the stent is such that the end of the stent where suture attachment of a graft is required is axially positioned so as to be reasonably accessible to the surgeon so as to enable and facilitate suture attachment.

Other and further objects of the present invention will become apparent to those skilled in the art upon a study of the following specification, appended claims, and accompanying drawings.

IN THE DRAWINGS

FIG. 1 is a front perspective view of a graft network employing the stented graft devices of the present invention, with this figure illustrating the stented grafts in place; and with the shaded areas showing where the stent has been inserted in the network for delivery of blood to a diseased coronary artery;

FIG. 2 is a front elevational view of one stent structure, illustrating a supply lumen together with a branch lumen, and with the cross-over between supply and branch lumens being shown as well, with the graft portion having been removed;

FIG. 3 is a front elevational view of a modified form of the cross-over of FIG. 2, and illustrating further the manner in which the graft is secured in place on the stent;

FIG. 4 is a front elevational view similar to FIG. 2 and illustrating a still modified form of stent, and with the graft portion being removed;

FIG. 5 is a front elevational view of a still further configuration for a stent, and being shown with the graft removed;

FIG. 6 is a top plan view of a stent designed for use at the distal end of the artificial graft, with a graft shown attached to the small end of the stent, with FIG. 6 being on a slightly reduced scale;

FIG. 7 is a side elevational view of the stent illustrated in FIG. 6, and shown with the graft portion removed;

FIG. 8 is a top plan view of a stent similar to that of FIG. 6, but with an oval configuration being employed for attachment to the aorta or vena cava;

FIG. 9 is a side elevational view of the stent apparatus of FIG. 8; and

DESCRIPTION OF THE PREFERRED EMBODIMENT

Figure 10:
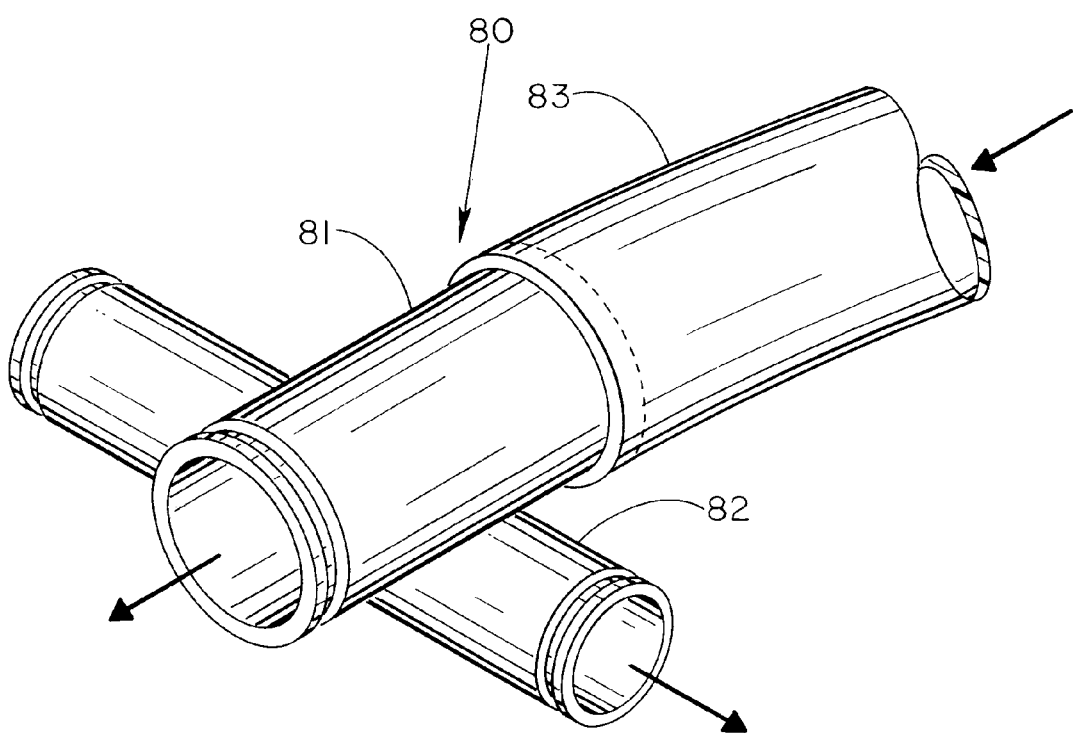
FIG. 10 is a front perspective view of an alternate form of stented graft device of the present invention.

In accordance with the preferred embodiment of the present invention, and with particular attention being directed to FIG. 1 of the drawings, the graft network generally designated 10 includes a graft segment 11 attached by suture to the aorta as at 12, and with segment 11 being, in turn, affixed to a stent in place in the system as at 13. Because of limitations of draftsmanship, the stent device does not appear in detail, but is in place with the branch lumen being in place in angularly disposed relationship along the shaded areas in coronary artery 14. A second graft segment is provided as at 16, which is operatively coupled and joined to the downstream supply side of stent 13, with the distal end of graft 16 having been previously coupled to stent shown at 18. Again, because of limitations of draftsmanship, stent 18 is in place between the shaded areas of coronary artery 19.

A further graft segment is provided as at 21, with graft segment 21 being sutured or otherwise secured to the distal end of the supply channel of stent 18. Stent 23, which has previously been affixed to graft 21, is appropriately secured to the surface of the superior vena cava and is utilized to provide a suitable means for receiving that portion of the blood flow from the network 10 which does not otherwise pass from the network to coronary arteries 14 and 19.

By way of example, the stents utilized in the example given above and interposed at 13 and 18 may be of a design selected from one of the stents illustrated in FIGS. 2, 3, 4 or 5. By way of explanation, and with attention being directed to FIG. 2 of the drawings, stent generally designated 30 is a dual lumen device which comprises a pair of lumens arranged in parallel axial relationship within tubular members 31 and 32. Member 31 functions as a supply lumen with tubular member 32 as a delivery member. Cross-over 33 is provided to meter an appropriate amount of blood flowing within supply tube 31 to tube 32. A graft, not shown, is permanently attached to stent 30, of a type as illustrated at 35 in FIG. 3. Sutures as shown at 36 are utilized, in place, in order to couple or otherwise secure graft 35 to the proximal end of member 31A. As is apparent from FIG. 1, an annular groove is formed within tubular members 31 and 32, particularly as shown at 38, in order to properly receive and retain suturing means therewithin.

It will be observed that tubular members 31 and 32 are offset, in an axial direction, one from the other. In this arrangement, the end shown adjacent annular groove 38 is arecessed and/or positioned beneath the corresponding suturing ring 39 in the delivery portion of stent 30. In this arrangement, therefore, the opposed ends of tubular member 31 projects beyond the corresponding terminal end of delivery tube 32, such as at 40 about the smaller delivery tube 32. Also, annular groove 41 is provided to accommodate suture attachment of the next adjacent graft segment, with the suture operation being undertaken in the course of the actual procedure. It will be observed that the axial positioning of the tubular members 31 and 32, one with respect to the other, is such that there is a significantly greater accessibility to end 40, than to the opposed end.

Inasmuch as the configurations of the individual stents illustrated in FIGS. 3, 4 and 5 are essentially the same as those of FIG. 2, similar reference numerals and identical suffixes will be employed. For example, reference numerals 31A, 32A, 39A, and 41A designate structure similar to that described in connection with FIG. 2 without the alphabetical suffix. The primary distinction between the structures of FIGS. 2 and 3 lies in the configuration of the cross-over member 43, with this member being positioned in angular relationship at an acute angle to the flow direction, rather than at a right angle as in the device of FIG. 2.

FIG. 4 is likewise similar in its structure to that of FIG. 2, with the exception being that in the arrangement of the cross-over to a branch lumen utilizing a separate conduit, a bore is formed between the juncture points of supply lumen 50 and delivery lumen 51, with the port being positioned securely within the juncture point, as at 52. The orifice size is such that appropriate flow may be achieved. Also, as indicated in connection with FIG. 3, similar structural features found in FIG. 4 are designated with the alphabetical suffix "B" as corresponding to those numeric elements of FIG. 2, including elements 38B, 40B, and 41B.

FIG. 5 is again similar in structure and function to that of FIG. 2, with the exception of the cross-over member shown at 55. Cross-over member 55 blends into delivery member 56, with flow being the same as that as illustrated and described in FIG. 2.

In the arrangement illustrated in FIG. 5, it will be noted that the axial length and positioning of the members 56 and 57 are generally coincidental, one with the other. Because of the axial offset provided as at 55, some limited relief is possible to enable the surgeon to suture a graft onto end 58, with a graft (not shown) already having been affixed and secured to end 59.

In certain applications, it may be appropriate to utilize tubular members which are arranged angularly, one to the other. In such an arrangement, the axial offset may be accomplished through the angular relationship of the individual tubular members. Such a configuration is present in the arrangement of FIG. 1.

With attention now being directed to the embodiments illustrated in FIGS. 6–9, it will be observed that a distal or terminal end of the artificial graft is provided in stent generally designated 60 (FIG. 6), with stent 60 including a body member 61 having a configured bore formed therein illustrated in phantom as at 62. Graft 63 is shown secured in place within annular groove 64 formed within the blood-receiving end of stent 61. Stent 61 is designed to be secured by conventional suture to the wall of the atrium or superior vena cava, with suture retaining flange 65 being provided for that purpose.

The stent generally designated 70 illustrated in FIG. 8 is similar to that of stent 60, with the exception of the configuration of the distal end 71. It will be observed that distal end 71 is of oval configuration, with this configuration making it possible for attachment to a vessel having an angular configuration to flow, with the oval configuration being designed to preserve the laminar flow which is desirably achieved throughout the extent of the graft network. As is illustrated in FIG. 9, sewing flange 72 is provided around the circumference of stent 70.

With attention now being directed to FIG. 10, the embodiment of the stented graft generally designated 80 includes a pair of individual tubular members 81 and 82 which are disposed in right angular relationship, one to the other. A graft 83 is coupled to one end of the tubing for the advantageous reasons as set forth above. Communication between tubing elements 81 and 82 is achieved through an appropriately positioned flow channel which communicates between the bores of members 81 and 82.

In performing procedures with the stented grafts of the present invention, the surgeon forms a longitudinal slit in the coronary artery where blockage is known to be present, with the slit being formed downstream from the point of blockage. Thereafter, one end of the tubular stent element is introduced into the coronary artery, and thereafter upon appropriate manipulation, the opposed end is introduced through the same slit. Thereafter, a suture needle is passed through the tissue under the stent, and in alignment with the recess formed in the outer surface of the stent, with the suture then being brought up and ultimately tied. In certain instances, the suture procedure may include forming a continuous loop around the artery wall, and within the annular recess.

BIOCOMPATIBLE MATERIALS

As has been indicated, biocompatible materials are, of course, utilized in forming any and all of the components of the present invention. In fabricating the components for the present invention, and as previously indicated, biocompatible materials are selected. For the stent component, suitable materials may be selected from the group consisting of titanium, stainless steel, or plastics such as polytetrafluoroethylene, polyurethane, polyethylene, or the like. In certain instances, when a metal is employed, those portions of the stent which are exposed may be coated with a suitable biocompatible coating.

As previously indicated, the graft portion may comprise a suitable biocompatible material such as, for example, Gortex™, a well-known and frequently utilized polytetrafluoroethylene-based material. Such materials are, of course, commercially available.

STENT CONFIGURATION

In most situations and for most applications, orifices and lumens in the delivery side are typically in the range of about 2 millimeters in diameter, although the requirements of individual patients may indicate slightly larger or smaller diameters. This diameter range has been found to preserve laminar flow, with this preservation being a desirable feature for maintaining continuity of blood flow. The lumen on the supply side of the stent is typically of greater diameter, with this diameter being adequate to accommodate the necessary blood flow. Also, in order to preserve the pressure throughout the supply network, the diameters of the lumens on the delivery side should remain in the range set forth above.

It will be appreciated, therefore, that the features of the present invention enable the surgeon to more effectively and expeditiously complete the preparation and attachment of a graft network to the vasculature of a patient, and with the design and configuration of the features of the present invention, in particular, being helpful in this enablement.

It will be further appreciated that the specific examples provided herein are for purposes of illustration only, and are not to be construed as a limitation upon the scope to which the present invention is entitled.

What is claimed is:

1. Means for creating a vascular graft network for surgical implantation for creating bypass blood flow in coronary arteries, and adapted to be received within the vascular system of the patient; said means comprising:

(a) a first and a second stented graft;
    (b) said first stented graft comprising a stent body with a pair of spaced-apart tubular elements, each having a distinct lumen formed therewithin and including one of a blood supply lumen or a delivery lumen, and with a cross-over lumen extending therebetween and providing for blood flow from said supply lumen to said blood delivery lumen;
    (c) said supply lumen having opposed proximal and distal graft link receiving blood flow ends, and with said proximal blood flow end having a graft link secured and affixed thereto, with said graft link being adapted to form a portion of said vascular graft network;
    (d) said delivery lumen being configured for direct implantation into a selected coronary artery at a location for delivering bypass blood flow from said supply lumen into said selected coronary artery; and
    (e) the opposed ends of said delivery lumen being axially offset from the opposed flow ends of said supply lumen, and with the distal end of said supply lumen extending axially beyond the adjacent end of said delivery lumen;
    (f) said second stented graft comprising a stent body having a graft link secured to the proximal end and adapted to receive a flow of blood from said first stented graft, said second stented graft adapted for application as a terminal device for said vascular graft network, and having means thereon for surgically joining the distal end of said second stented graft to the patient's vasculature system.

2. The means of claim 1 wherein said first stent body and said second stent body are fabricated from titanium.

3. The means of claim 1 in that the distal blood flow end of said second stented graft is coupled to the atrium or vena cava of the patient.

* * * * *